United States Patent [19]

Gabbay

[11] Patent Number: 4,596,028
[45] Date of Patent: Jun. 17, 1986

[54] GENERAL PURPOSE X-RAY TUBE FOR STEREOGRAPHY

[75] Inventor: Emile Gabbay, Paris, France
[73] Assignee: Thomson-CSF, Paris, France
[21] Appl. No.: 520,710
[22] Filed: Aug. 5, 1983

[30] Foreign Application Priority Data

Aug. 6, 1982 [FR] France ................................ 82 13801

[51] Int. Cl.⁴ .................... A61B 6/02; H01J 35/00; H01J 35/06
[52] U.S. Cl. .................................. 378/41; 378/134
[58] Field of Search ........................ 378/41, 42, 134

[56] References Cited

U.S. PATENT DOCUMENTS 3,389,253  6/1968  Kok ..................................... 378/134
4,287,420  9/1981  Yamamura et al. .................. 378/41

FOREIGN PATENT DOCUMENTS 55-151795  11/1980  Japan ................................... 378/138

Primary Examiner—Alfred E. Smith
Assistant Examiner—T. N. Grigsby
Attorney, Agent, or Firm—Oblon, Fisher, Spivak, McClelland & Maier

[57] ABSTRACT

The invention provides a general purpose X-ray tube for stereography usable in the field of radiology. An X-ray tube of the invention comprises at least three independent cathodes, each allowing a source of an X-ray beam to be obtained. These sources are at different distances from each other, so as to form working pairs allowing stereographic pictures to be taken of a subject with different enlargement values.

6 Claims, 1 Drawing Figure

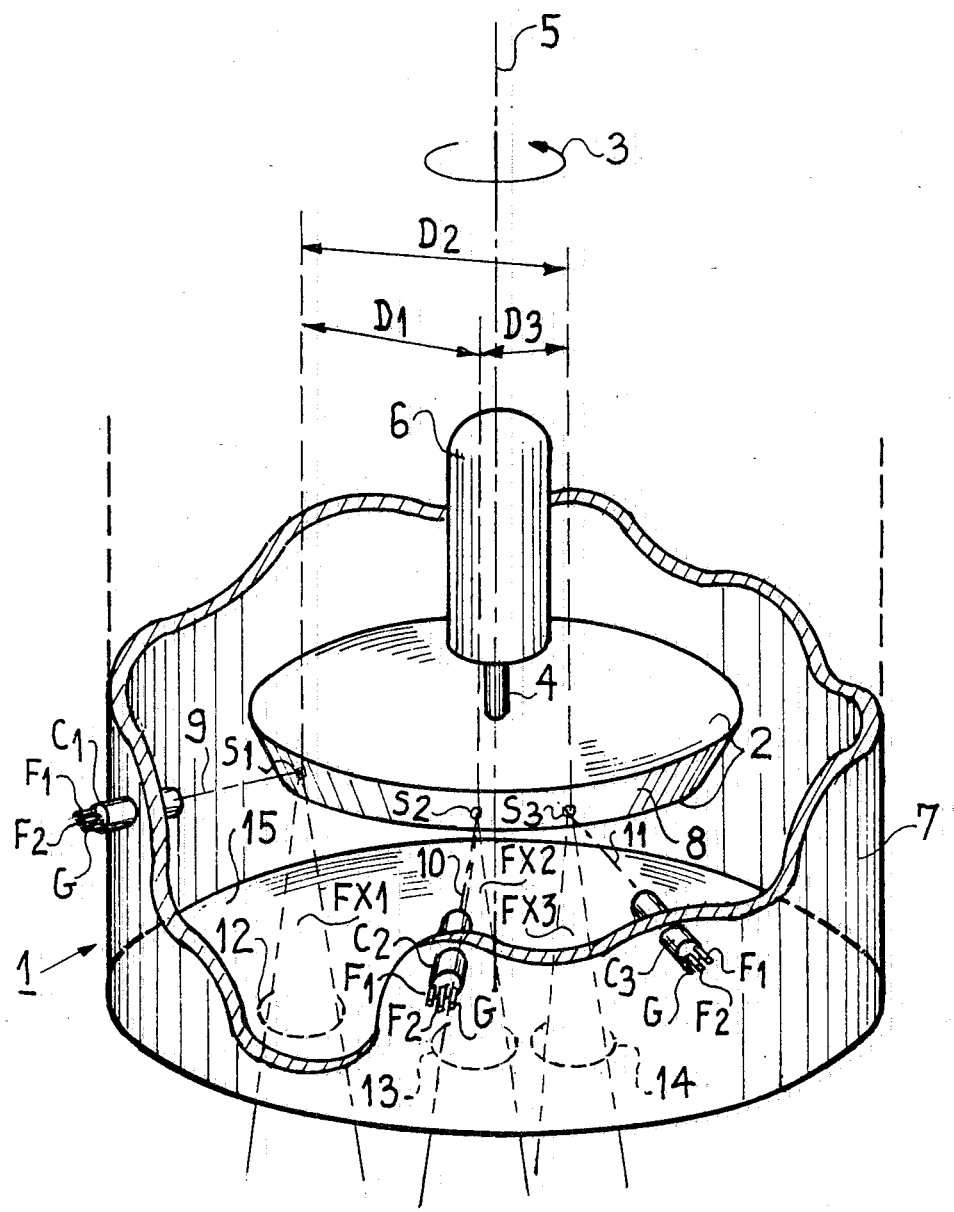

GENERAL PURPOSE X-RAY TUBE FOR STEREOGRAPHY

BACKGROUND OF THE INVENTION

1. Field of the Invention

The present invention relates to a general purpose X-ray tube for stereography, usable in the field of radiology and more particularly in that of radiodiagnosis.

2. Description of the Prior Art

The stereographic effect is obtained by radiographing the same subject from two sources, located independently in space, each defining an image or picture of the object seen at a different incidence. Stereoscopic viewing of this subject is obtained by regarding these two images in binocular vision, i.e. each of the images is regarded independently by each of the two eyes; the two retinal perceptions are conveyed by the optic nerve to the brain, which which merges them together and provides three-dimensional perception thereof.

The quality of this three-dimensional perception is related to the conditions of taking the pictures and to the conditions in which these pictures are viewed. Thus, in a first case, in which pictures are taken with an object in the vicinity or in contact with a film, determining a minimum enlargement, three-dimensional viewing reproducing this object under the best conditions is obtained when:

(a) a distance between the two sources is equal to the distance between the eyes, i.e. approximately 65 mm;

(b) when an "eyes-pictures" distance on viewing is equal to a "source-pictures" distance when the pictures are taken.

This poses a problem because, in practice, for better observation of details, the "eyes-pictures" distance on viewing is less than the "source-pictures" distance when the pictures are taken. Modifying the picture taking conditions, for example, effected in a first direction, is likely to re-establish the quality of this three-dimensional vision; but this modification must be exerted in a direction opposite the first one when, so as to obtain a larger enlargement, the object is moved away from the film for taking the pictures.

SUMMARY OF THE INVENTION

The X-ray tube of the present invention allows stereographic pictures to be taken, viewable from a distance current in practice while maintaining the quality of the three-dimensional vision, and allowing a maximum of different enlargement values with a minimum of sources.

According to the invention, a general purpose X-ray tube for stereography, comprising a rotary anode is characterized in that it further comprises n independent cathodes, n being at least equal to three, disposed so as to allow an anode target to be formed, n sources of an X-ray beam spaced apart from each other by a different distance, any two of these sources being associated so as to form a working pair chosen as a function of the distance apart of the sources which form it, these latter being formed alternately so that the X-ray beam which they generate allows stereographic pictures of a subject to be taken, compatible with a chosen enlargement value.

BRIEF DESCRIPTION OF THE DRAWINGS

The invention will be better understood from the following description and the single accompanying FIGURE.

This FIGURE shows schematically, in a perspective view, characteristic elements of an X-ray tube 1 in accordance with the invention.

DETAILED DESCRIPTION OF THE INVENTION

The tube 1 comprises a rotary anode 2, rotated in the direction of arrow 3 for example, about a first axis 5 perpendicular to the plane of the rotary anode 2 and passing through a center 4 thereof. This rotation is conventionally obtained by means of a motor formed of a rotor 6 and a stator (not shown) disposed so as to take into account electric insulation and sealing problems well known to a man skilled in the art. The rotary anode 2 has a truncated cone shape, the truncated cone forming an anode target 8.

A case 7, shown partially for the sake of clarity of the drawing, supports a first, a second and a third cathode $C_1, C_2, C_3$, disposed so as to be contained in the plane of rotation of the rotary anode 2; these cathodes are each capable of emitting an electronic beam (not shown) along an axis 9, 10, 11 also included in the plane of rotation of the anode and oriented so as to intercept the first axis 5.

A focal point formed by the impact of each electron beam on the anode target 8 forms a first, a second and a third source $S_1, S_2, S_3$ of an X-ray beam $FX_1, FX_2, FX_3$. These cathodes $C_1, C_2, C_3$ are disposed so that the sources $S_1, S_2, S_3$ which they define are at different distances $D_1, D_2, D_3$ from each other.

This forms a non limiting example of a tube 1 in accordance with the invention, such a tube being able to comprise a greater number of cathodes (not shown) disposed so as to allow as many sources $S_1, S_2, S_3, \ldots, S_n$ to be formed of an X-ray beam $FX_1, FX_2, FX_3, \ldots, FX_n$, situated at different distances $D_1, D_2, D_3, \ldots, D_n$ from each other.

As was mentioned in the preamble, three-dimensional viewing requires, when the pictures are taken, the alternating use of a first and a second source of the same kind, located at different points representing a given distance, these two sources forming a working pair. In a tube 1 in accordance with the invention, such a working pair is obtained by the association of any two of these three sources $S_1, S_2, S_3$, the working pair thus formed being singularized by a first or a second or a third distance $D_1, D_2, D_3$ between the two sources which form it. This association of two of these sources $S_1, S_2, S_3$ is provided by a control (not shown) applied to those of the cathodes $C_1, C_2, C_3$ charged with forming respectively an X-ray source $S_1, S_2, S_3$.

For that, each cathode is independent and conventionally comprises the following elements (not shown):

an electron generating filament to which a heating current is applied by means of a first and a second output terminal $F_1, F_2$;

an element called grid, allowing the electrons to pass or not towards the rotary electrode 2, to which the abovementioned control is applied through a third output terminal G. This control consists of a voltage, biassing the grid negatively with respect to the filament so as to block the electrons coming from the filament; the removal of this biassing voltage allows the electron beam to be formed.

Cathodes $C_1, C_2, C_3$ are thus independent, able to be controlled independently of each other and to form the X-ray sources $S_1, S_2, S_3$ of same characteristics in a desired order: the filament of each cathode corresponding to a working pair able to be permanently supplied with power.

Thus, a first working pair may be obtained by the association of the first and the second sources $S_1, S_2$ spaced apart by the first distance $D_1$; a second working pair formed by the first and the third sources $S_1, S_3$ corresponds to the second distance $D_2$ and a third pair formed by the second and the third sources $S_2, S_3$ corresponds to the third distance $D_3$.

This forms an important feature of the invention which allows, in the non limiting example described, three working pairs $S_1$-$S_2, S_1$-$S_3, S_2$-$S_3$ to be obtained whereas with two cathodes only one working pair may be obtained.

A tube 1 in accordance with the invention may comprise n cathodes $C_1, C_2, C_3, \ldots, C_n$ for obtaining a number of such working pairs determined by the following law:

$$C_n^2 = \frac{n!}{2!(n-2)!}$$

where $C_n^2$ represents the number of possible pair combinations for n cathodes.

Since these working pairs each correspond to a different distance $D_1, D_2, D_3$ they each allow stereographic pictures to be taken of a subject (not shown) with a different enlargement value.

The following table gives by way of non limiting example the value of distances $D_1, D_2, D_3$ corresponding to each working pair $S_1$-$S_2, S_2$-$S_3$, $S_1$-$S_3$ as well as enlargement values compatible with each working pair:

| WORKING PAIR | DISTANCE | ENLARGEMENT |
|---|---|---|
| 1st pair source $S_1$-$S_2$ | $D_1 = 45$ mm | Medium enlargement: 1.2 to 1.7 for example |
| 2nd pair source $S_1$-$S_3$ | $D_2 = 70$ mm | Zero or low enlargement: object in contact with the film or practically in contact therewith |
| 3rd pair source $S_2$-$S_3$ | $D_3 = 20$ mm | High enlargement: 1.7 to 3 for example |

In the non limiting example of the description, the case 7 is made from metal and cathodes $C_1, C_2, C_3$ are at the same potential as this case; the radiation beams $FX_1, FX_2, FX_3$ emerge through outlet windows 12, 13, 14 shown with broken lines in the FIGURE, these outlet windows being disposed on a face 15 of case 7 parallel to the plane of the rotary anode 2. The power supply for the tube may be of the monopolar type, which facilitates switching of cathodes $C_1, C_2, C_3$, these then being at ground potential and the rotary anode 2 at the high positive voltage.

An X-ray tube 1 in accordance with the invention is of the greatest interest for stereography, because of its multiple possibilities which allow it to be applied to radiodiagnosis, in cases for example such as: cranial vascular and abdominal cases as well as cases of fine fractures.

I claim:

1. A general purpose X-ray tube for stereography, comprising:
    a rotary anode;
    n independent cathodes, of the same type and whose focal points are the same size, and with n being at least equal to three, disposed so as to allow the formation on an anode target of n sources of an X-ray beam spaced apart from each other by a different distance, any two of said sources being associated to as to form a working pair chosen as a function of the distance apart of the sources which form it, these latter being formed alternately so that the X-ray beam which they generate allows stereographic pictures to be taken of a subject compatible with a chosen enlargement value.

2. The X-ray tube as claimed in claim 1, wherein said anode target is in the form of a truncated cone.

3. The X-ray tube as claimed in claim 1, wherein each working pair allows compatible stereographic pictures to be taken with a different enlargement.

4. The X-ray tube as claimed in claim 1, further comprising a metal case supporting said cathodes.

5. The X-ray tube as claimed in claim 4, wherein said cathodes are at the same potential as the metal case.

6. A general purpose X-ray tube for stereography, comprising;
    a rotary anode;
    n independent cathodes, n being at least equal to three, disposed so as to allow the formation on an anode target of n sources of an X-ray beam spaced apart from each other by a different distance, any two of said sources being associated so as to form a working pair chosen as a function of the distance apart of the sources which form it, these latter being formed alternately so that the X-ray beam which they generate allows stereographic pictures to be taken of a subject compatible with a chosen enlargement value; a metal case supporting said cathodes; and means for maintaining said cathodes at the same potential as said metal case.

* * * * *